(12) United States Patent
McKee et al.

(10) Patent No.: US 9,220,798 B2
(45) Date of Patent: Dec. 29, 2015

(54) PRESSURIZED SCREW SYSTEM USING AIR LOCKS FOR WASTE DISPOSAL

(71) Applicant: BioSafe Engineering, LLC, Brownsburg, IN (US)

(72) Inventors: Randall G. McKee, Mooresville, IN (US); Phillip Mervis, Indianapolis, IN (US); Brandon Ross, Brownsburg, IN (US)

(73) Assignee: BioSafe Engineering, LLC, Indianapolis, IN (US)

(*) Notice: Subject to any disclaimer, the term of this patent is extended or adjusted under 35 U.S.C. 154(b) by 269 days.

(21) Appl. No.: 13/765,711

(22) Filed: Feb. 13, 2013

(65) Prior Publication Data
US 2014/0224905 A1 Aug. 14, 2014

(51) Int. Cl.
*B02C 23/20* (2006.01)
*A61L 2/07* (2006.01)
*B02C 19/00* (2006.01)
*B09B 3/00* (2006.01)
*A61L 11/00* (2006.01)

(52) U.S. Cl.
CPC ............. *A61L 2/07* (2013.01); *B02C 19/0075* (2013.01); *B02C 23/20* (2013.01); *B09B 3/0075* (2013.01); *B09B 3/0091* (2013.01); *A61L 11/00* (2013.01)

(58) Field of Classification Search
CPC .... B02C 23/20; B02C 19/0075; A61L 11/00; A61L 2/07; B09B 3/0075; B09B 3/0091
USPC ............... 241/23, 65–67, 236, 606, 260.1
See application file for complete search history.

(56) References Cited

U.S. PATENT DOCUMENTS

| 5,190,226 A | 3/1993 | Holloway |
| 6,588,690 B1 * | 7/2003 | Koenig ........................ 241/65 |
| 7,347,391 B2 * | 3/2008 | Michalek et al. ............ 241/23 |
| 2008/0213124 A1 | 9/2008 | Hengl |

FOREIGN PATENT DOCUMENTS

| GB | 2 320 192 | 6/1998 |
| WO | WO 93/06418 A1 | 4/1993 |
| WO | WO 01/68152 A2 | 9/2001 |

OTHER PUBLICATIONS

European Search Report dated Jul. 25, 2014, in European Ptent Application No. 14020014.8, pp. 1-6.

* cited by examiner

*Primary Examiner* — Mark Rosenbaum
(74) *Attorney, Agent, or Firm* — Woodard, Emhardt, Moriarty, McNett & Henry LLP

(57) ABSTRACT

Hazardous waste is treated by shredding and then passing the material through an enclosure by means of a conveyor through direct steam impingement. The enclosure is maintained at a pressure greater than or equal to atmospheric pressure in order to maintain steam temperature at or above 212° F. Pressure locks are positioned at an inlet and discharge of the enclosure. The pressure locks allow transport of waste material into and out of the enclosure while maintaining a pressure differential between the interior and exterior of the enclosure.

14 Claims, 4 Drawing Sheets

PRESSURIZED SCREW SYSTEM USING AIR LOCKS FOR WASTE DISPOSAL

BACKGROUND

The present invention relates generally to waste treatment and more particularly to methods and apparatus' for potentially infectious waste treatment which is operable at varying atmospheric pressures.

Often biohazardous materials or pests must be safely disposed of. For example, biohazardous materials exist at commercial or governmental waste disposal plants, on-site at hospitals, and other medical facilities. Additionally, infectious or potentially infectious waste and pests which threaten agriculture and ecological systems can enter U.S. borders from international flights, international ships, and international arrivals of private water crafts. These types of wastes are often referred to as quarantine wastes. Disposing of biohazardous and/or quarantine wastes and pests on-site can prevent expensive transportation costs and risks associated with such costs. On-site disposal can also be a powerful tool in the context of hazardous material intercepted at U.S. ports of entry. Fast and reliable disposal of infectious or potentially infectious material can mitigate or avoid catastrophic outbreaks.

When treating infectious waste for disposal, it is important to ensure that the ultimate waste product which is to be discarded is free from pathogenic microorganisms. It is also desirable, and in some instances required by law, to render the waste material in a condition such that individual components (e.g. disposable syringes, bandages, body fluid receptacles and body parts) are unrecognizable.

Potential waste disposal methods include incineration, autoclaving, microwaving or other non-incineration treatment methods with autoclaves and incineration being the most commonly used. Environmental regulations have severely limited the use of incineration for waste disposal, and alternative treatment methods (primarily steam autoclaving) are often used as an alternative. Typical problems associated with gravity and vacuum autoclaves include the requirement for large volume high pressure (>1 BAR) steam. These pressure vessels require initial and on-going certifications to ensure pressure vessel integrity; cooling towers to cool the autoclave at the end of the cycle; batch only (not continuous feed) systems. Treated waste material from the high pressure autoclaves is very wet and heavy causing increased disposal costs. Some of the available methods are not entirely effective at destroying pathogenic organisms. Some methods (e.g. autoclaving) are "batch" treatment systems which are inefficient in operation. Batch treatment systems limit treatment throughput and consequently require storage of untreated materials while the batch is "cooking", creating additional needs for users. Most batch treatment methods require equipment which tends to be expensive to install and both expensive and labor intensive to operate. Further problems with current methods include foul odors, noxious gases, liquids, and solid particles which are exhausted to the atmosphere or discharged to sanitary sewage systems. For example, certain plastics when in the semi-solid state can release volatile organic compounds (VOC's) which are hazardous to the health and the environment.

Regulations require treatment temperatures of 212° F. for a specified period of time. Current steam sterilization systems designed to operate at atmospheric pressures are unable to operate at the correct temperatures when the system is located at differing elevations above sea level. In most thermodynamic processes the temperature of the system is directly proportional to the pressure of the system such that changes in the system pressure result in changes to the system temperature. For example, an atmospheric steam treatment system located at 5000 ft MSL operates in a relatively reduced pressure and correspondingly the operating temperature is reduced, in some cases below 212° F.

Thus, there is a need for continuous feed (not batch process) steam sterilization systems which are capable of operating at increased elevations while maintaining a gage pressure which is equivalent to or greater than atmospheric pressure at sea level in order to maintain a requisite system temperature of 212° F.

SUMMARY

The waste disposal system disclosed herein provides a novel way to treat potentially infectious waste. The waste disposal system utilizes a combination of continuous throughput (not a batch process), physical destruction, elevated temperatures, and low-pressure steam to remove biohazards associated with hazardous waste materials (e.g. to steam sterilize microbes). Through use of pressurized steam, it is possible to eliminate viable microorganisms entirely. The apparatus delivers a product which is bulk reduced by up to 90% (compact), held safely in conventional bulk trash containers, and transported in conventional trash trucks or roll-off containers for disposal in landfills or similar facilities. The treatment system also incorporates a sub-system that allows for the introduction of an odor control chemical to curtail obnoxious odors as the system operates.

The waste disposal system includes several components used to introduce and treat the infectious waste in a continuous manner (high efficiency operation), causing the waste materials to no longer be infectious. The system includes a steam chamber having an elongated enclosure with pressure locks positioned at both ends. A rotatable conveyor is positioned within the enclosure. A feed hopper and optional shredder are positioned at one end of the enclosure. A discharge area is positioned at the other end of the enclosure.

The feed hopper receives waste material and feeds it into the shredder. The optional shredder physically breaks down the waste material prior to entering the enclosure. An odor control chemical solution is optionally applied to the waste once the material is past the shredder.

A rotatable conveyor is positioned throughout the length of the enclosure. The rotatable conveyor is driven by an external driving means. A series of steam injection valves are positioned within the enclosure and are configured to deliver steam directly to the shredded waste materials being transported by the conveyor. A steam jacket is positioned around a portion of the enclosure. Waste materials that travel through the enclosure are subjected to steam at a minimum temperature of 212° F. or greater for a specified period of time.

An inlet pressure lock is positioned at the entrance end of the enclosure and includes a top inlet valve and a bottom inlet valve. Positioned at the other end of the enclosure (and rotating conveyor), is a discharge pressure lock having a top discharge valve and a bottom discharge valve. The two valves at each end of the rotating conveyor constitute the pressure lock at each end. In one configuration the valves are sliding type valves which are engaged by a drive motor. The sliding type valves are planar structures slidable to a position which sealingly isolates each side of the valve from the opposite side.

In a first configuration the entrance pressure lock is configured to receive waste material at atmospheric pressure. Simultaneously, the exit pressure lock is configured to receive waste material at gage pressure (or the interior pressure of the chamber). The pressure locks can be activated and moved from the first configuration to a second configuration. In the second configuration, the entrance pressure lock is configured to convey waste material to the conveyor and the exit pressure lock is configured to convey waste material through a discharge.

The waste disposal system maintains a desired pressure within the enclosure by proper operation of the pressure locks. As used in the pressure locks, the valves are capable of creating a pressure locked area positioned between the interior of the enclosure and the exterior of the enclosure. Material can be transferred between the interior and the exterior while substantially maintaining a pressure differential between the interior and exterior. In every operating instance, at least one of the two stackable valves at each end of the rotating steam conveyor is closed. At no point during operation are both valves at a given end (inlet end or discharge end) open at the same time. In that way, the valves provide a continuous pressure seal between the interior of the enclosure and the exterior atmosphere. The system operates in an essentially continuous manner without interruption caused by the pressure lock valves switching positions.

During processing, the waste material moves from the inlet pressure lock, engages with the conveyor, and travels through the enclosure in response to the driving force of the conveyor. The waste is exposed to a high temperature and treated with low pressure (<1 BAR) steam while traveling through the enclosure. The helical type conveyor causes the waste material to be agitated and maximally exposed to steam. This process continues while the pressure locks operate to move material between the interior and exterior of the enclosure.

The combination of the inlet pressure lock and the discharge pressure lock allow the steam within the enclosure to be maintained at a pressure which is higher than the exterior atmospheric pressure condition. Correspondingly, the temperature of the steam is dependent upon the internal pressure of the enclosure rather than the exterior atmospheric pressure. The waste disposal system can be operated at a pressure and temperature which is independent of the atmospheric pressure at the location of the waste disposal system. For example, the waste disposal system can be operated in areas of Colorado where the elevation can be more than 5,000 ft above sea level while always maintaining internal waste temperatures at or above 212° F. (100° C.).

In an alternative example, the waste disposal system can include rotary valves in the inlet and discharge pressure locks. The rotary valves are rotatable about an axis through various configurations in which the pressure lock is alternately exposed to the exterior atmosphere and the interior of the steam chamber. The rotary valves provide a pressure seal between the interior of the steam chamber and the exterior atmosphere while facilitating movement of waste material into and out of the steam chamber. The rotary valves provide the same functionality to the waste disposal system as the sliding valves and can be similarly advantageous. The rotary valves may be utilized as a mechanical feeding means without ever exposing the interior of the enclosure directly to atmospheric pressure.

Further forms, objects, features, aspects, benefits, advantages, and embodiments of the present disclosure will become apparent from a detailed description and the drawings provided herewith.

DESCRIPTION OF THE SELECTED EMBODIMENTS

Figure 1:
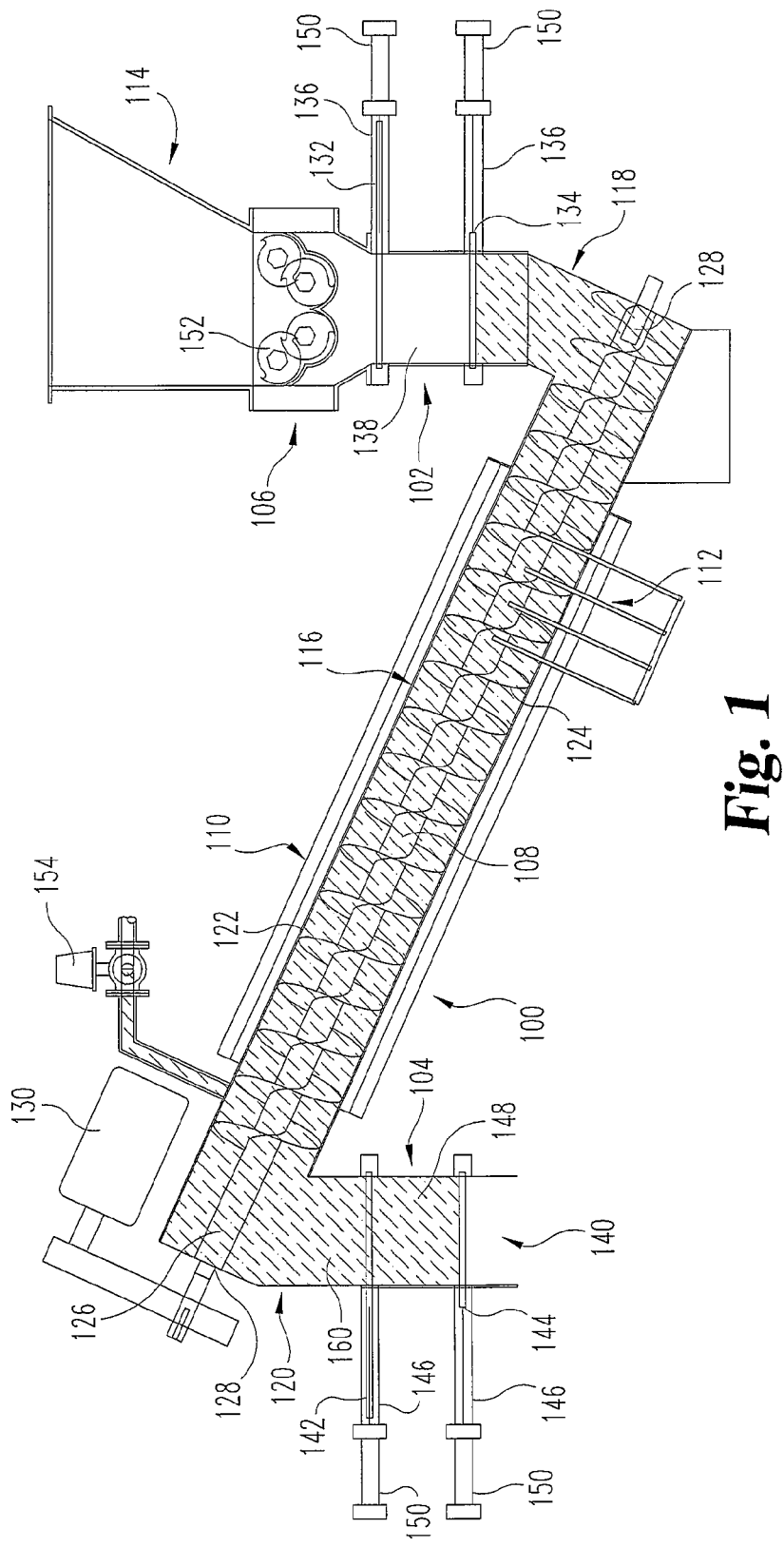
FIG. 1 is a cross-sectional illustrative view of a waste disposal system with an inlet pressure lock having an open top inlet valve and a closed bottom inlet valve and a discharge pressure lock having an open top discharge valve and a closed bottom discharge valve.

For the purpose of promoting an understanding of the principles of the disclosure, reference will now be made to the examples illustrated in the drawings and specific language will be used to describe the same. It will nevertheless be understood that no limitation of the scope of the disclosure is thereby intended. Any alterations and further modifications in the described examples, and any further applications of the principles of the disclosure as described herein are contemplated as would normally occur to one skilled in the art to which the disclosure relates. Certain examples of the disclosure are shown in great detail; although it will be apparent to those skilled in the relevant art that some features that are not relevant to the present disclosure may not be shown for the sake of clarity.

A waste disposal system for disposing of infectious or potentially infectious waste materials is disclosed herein. The system includes a chamber 100 having an inlet pressure lock 102 at one end and a discharge pressure lock 104 at another end (FIG. 1). An optional shredder 106 is positioned adjacent to the inlet pressure lock 102. A feed hopper 114 is positioned adjacent to the shredder 106. Positioned within the chamber 100 is a conveyor 108. A steam jacket 110 is positioned circumferentially around an outside area of the chamber 100. Positioned within the chamber 100 are injectors 112.

As a general summary of the waste disposal system, the system destroys and decontaminates waste material by subjecting the waste material directly to moist steam heat in a pressurized environment. Optionally, a shredding apparatus is used in combination with the system. Waste material is placed into the feed hopper 114 which feeds the material into the shredder 106. The waste material enters the inlet pressure lock 102 from the shredder 106. The inlet pressure lock 102 continuously seals the entrance to the chamber 100. The inlet pressure lock 102 is activated, fluidly isolates the waste material from the exterior of the enclosure, and facilitates introduction of the waste material into the chamber 100. The conveyor 108 causes the waste material to travel through the chamber 100 while undergoing agitating motion. The waste material is subjected to steam supplied from the injectors 112 and heat from the steam jacket 110. At an exit of the chamber 100, the waste material enters the discharge pressure lock 104. The discharge pressure lock 104 continuously seals the exit from the chamber 100. The discharge pressure lock 104 is activated, fluidly isolates the waste material from the chamber 100, and facilitates movement of the waste material out of the waste disposal system.

The waste disposal system includes several components which are described with further details herein. The chamber 100 includes an elongated enclosure 116 having an inlet opening 118 at one end for receiving waste material and a discharge opening 120 at its opposite end for delivering treated waste material. The elongated enclosure 116 has a cylindrical inner wall 122.

The conveyor 108 extends through the elongated enclosure 116 between the inlet opening 118 and the discharge opening 120. The conveyor 108 is preferably a helical screw type conveyor, or auger-type conveyor, having a helical blade 124 which is attached to a shaft 126. The helical screw includes continuous helical flights (Archimedes spiral) along the majority of the shaft 126. The conveyor 108 is rotatably mounted at hubs 128 near the inlet opening 118 and the discharge opening 120. The hubs 128 can include sealed bearings or bushings and provide an atmospheric seal between the exterior atmosphere and the interior of the chamber 100. The conveyor 108 fits into the elongated enclosure 116 with a small clearance between its blade 124 and the inner wall 122 of the enclosure 116. The conveyor 108 is driven by a conveyor drive 130 which is rotatably connected to the shaft 126 by a chain and gears or other means. The conveyor drive 130 imparts rotational motion to the conveyor 108. The rotatability and helical shape of the conveyor 108 provides transport of waste material from the inlet opening 118 through the enclosure 116 to the discharge opening 120.

In the FIG. 1 example, the inlet pressure lock 102 is positioned between the shredder 106 and the inlet opening 118. The inlet pressure lock 102 facilitates temporary storage and passage of waste material from the shredder 106 through the inlet opening 118 and into the chamber 100. The inlet pressure lock 102 includes a top inlet valve 132 and a bottom inlet valve 134. The top inlet valve 132 is positioned adjacent to a shredder outlet of the shredder 106. The bottom inlet valve 134 is positioned adjacent to the inlet opening 118. In some embodiments, the top inlet valve 132 and bottom inlet valve 134 are slide valves which are slidable between open and closed positions. The inlet pressure lock 102 includes slide channels 136. The top inlet valve 132 and the bottom inlet valve 134 are movable between the open and closed positions along the slide channels 136. The top inlet valve 132 provides a reciprocating fluid seal between the shredder 106 and an interior 138 (acting as a plenum to collect waste) of the inlet pressure lock 102. Similarly, the bottom inlet valve 134 provides a reciprocating fluid seal between the chamber 100 and the interior 138 of the inlet pressure lock 102.

The discharge pressure lock 104 is positioned between the discharge opening 120 and a discharge exit 140. The discharge pressure lock 104 facilitates temporary storage and passage of treated waste material from the discharge opening 120 to the discharge exit 140. The discharge pressure lock 104 functions similarly to the inlet pressure lock 102 and includes a top discharge valve 142 and a bottom discharge valve 144. The top discharge valve 142 is positioned adjacent to the discharge opening 120. The bottom discharge valve 144 is positioned adjacent to the discharge exit 140 (or adjacent to an inlet of the discharge exit 140). In some embodiments, the top discharge valve 142 and the bottom discharge valve 144 are slide valves which are slidable between open and closed positions. The discharge pressure lock 104 includes slide channels 146. The top discharge valve 142 and the bottom discharge valve 144 are movable between open and closed positions along the slide channels 146. The top discharge valve 142 provides a reciprocating fluid seal between the discharge opening 120 and an interior 148 (acting as a plenum to collect waste) of the discharge pressure lock 104. Similarly, the bottom discharge valve 144 provides a reciprocating fluid seal between the interior 148 and the discharge exit 140.

The inlet and discharge valves of the inlet pressure lock 102 and the discharge pressure lock 104 can be any of a variety of types of industrial sliding valves which are known in the art and suitable for the present application. Such valves are commercially available and capable of providing a reciprocating fluid seal as described herein. One example of such a valve is the BC (SER.90) Square Port Knife Gate Valve by Orbinox, which can be incorporated into the system described herein.

The valves of the inlet pressure lock 102 and the discharge pressure lock 104 are each engaged by a driver 150. The drivers 150 provide translational motion to each of the valves and cause the valves to move between open positions and closed positions. The drivers 150 can be electric motors, hydraulic motors, or any of a number of devices which are known in the art.

The optional shredder 106 can be any make and configuration which is suitable for shredding the waste material. The shredder 106 generally utilizes cooperative rotating cutters 152 which shred waste material. Shredded waste material is reduced in size and has increased overall surface area which enhances steam penetration. The shredder 106 can be made in a variety of configurations which can be selected depending on the materials to be handled. For example, it can include a one-shaft, two-shaft or four-shaft shredder, or plural two-shaft shredders or any of a variety of shredder configurations. The shredder 106 includes the feed hopper 114 which is connected to a top portion of the shredder 106. The feed hopper 114 includes a necked-down shape such that the portion attached to the shredder 106 is smaller than the opening of the feed hopper 114. A shredder outlet is positioned at the base of the shredder 106 which is adjacent to the top inlet valve 132 of the inlet pressure lock 102.

One or more conduits are connected from a low pressure steam source to the interior of the enclosure 116 for the purpose of bringing steam into direct contact with waste material. The chamber 100 includes a plurality of injectors 112 which are fluidly connected to the conduits. Four injectors 112 are shown in FIG. 1, however there can be greater or fewer injectors 112. The injectors 112 are spaced from one another in the longitudinal direction at locations between the inlet opening 118 and the discharge opening 120. Additional injectors 112 can be added in the longitudinal direction as well as circumferentially around the enclosure 116. The injectors 112 are positioned to carry steam to the waste material at multiple locations within the chamber 100 such that the waste material is exposed multiple times to a directly impinging source of steam. The steam source can be any suitable source of steam such as a boiler or steam generator. The conduits can be arranged in a variety of configurations with respect to the connectivity of the injectors 112 through the conduits to the steam source. For example, the injectors 112 can each be configured to simultaneously provide both steam and chemical(s) for odor control. The arrangement can also be configured so that the injectors 112 carry either solely steam or a combination of steam and odor control chemical(s).

The steam jacket 110 surrounds a portion of the enclosure 116. The steam jacket 110 has an inner area defined by an inner wall and an outer wall and is capable of holding steam. The steam jacket 110 receives steam from the same steam source that supplies steam to the injectors 112. The steam jacket 110 abuts an outer surface of the enclosure 116 or, alternatively, the steam jacket 110 is integral with the enclosure 116. The steam jacket 110 maintains the temperature of the steam from the steam source (typically 240-245 degrees F.) (<1 BAR pressure) and provides a heat source to the interior of the chamber 100.

A pressure relief valve 154 is incorporated into the chamber 100. The pressure relief valve 154 is fluidly connected with the interior of the chamber 100 and is capable of maintaining an internal pressure of the chamber 100. The pressure relief valve 154 can be any type which is suitable for engaging and releasing pressure within a vessel when a defined internal pressure is exceeded.

The waste disposal system described herein provides a novel way to treat waste materials. Previous systems included an auger operating at atmospheric pressure or reduced pressure inside of an enclosure. The new system provides for a pressurized treatment system allowing for higher internal temperatures than those achieved under atmospheric pressure. The system does not require an ANSI pressure rated vessel because the system does not operate at pressures greater than 15 psig (1 BAR). However, the system operates at pressures which are sufficient to maintain temperatures equal to or greater than 212° F. under any and all circumstances. Additionally, unlike higher pressure, high temperature treatment systems, the present system is designed to avoid melting plastics which when in the molten or semi-solid state can release volatile organic compounds (VOC's) which are hazardous to the health and the environment.

The above characteristics are achieved through use of the inlet pressure lock 102 and the discharge pressure lock 104, which provide a way for waste material to enter and exit the chamber 100 while maintaining a pressure differential between the interior of the chamber 100 and the exterior atmosphere. Accordingly, the valves are positionable in various configurations which achieve and maintain a pressure differential between atmospheric pressure and the internal pressure of the chamber 100 while simultaneously facilitating movement of waste material through the pressure locks. At all times during operation, at least one of the valves in each pressure lock is closed so that the interior of the chamber 100 is at all times fluidly sealed from the exterior.

For example, when the top inlet valve 132 is in the closed position (FIG. 2), the shredder 106 is fluidly sealed from the interior 138, and the interior 138 is also sealed from the surrounding atmosphere. When the top inlet valve 132 is in a closed position and the bottom inlet valve 134 is in the open position (FIG. 2), the inlet pressure lock 102 is configured to transfer waste material through the inlet opening 118.

When the bottom inlet valve 134 is in the closed position (FIG. 1), the interior 138 is fluidly sealed from the chamber 100. When the bottom inlet valve 134 is in the closed position and the top inlet valve 132 is in the open position (FIG. 1), the interior 138 is fluidly sealed from the chamber 100 and the inlet pressure lock 102 is configured to receive waste material from the shredder 106.

When the top discharge valve 142 is in a closed position (FIG. 2), the chamber 100 is fluidly sealed from the interior 148. When the top discharge valve 142 is in a closed position and the bottom discharge valve 144 is in the open position (FIG. 2), the discharge pressure lock 104 is configured to transfer waste material through the discharge exit 140.

When the bottom discharge valve 144 is in the closed position (FIG. 1), the interior 148 is fluidly sealed from the discharge exit 140, and the interior 148 is also sealed from the surrounding atmosphere. When the bottom discharge valve 144 is in the closed position and the top discharge valve 142 is in the open position (FIG. 1), the interior 148 is fluidly sealed from the discharge exit 140, and the discharge pressure lock 104 is configured to receive treated waste material through the discharge opening 120. In this way, a pressure differential is always maintained between atmospheric pressure and the internal pressure of the chamber 100.

Figure 2:
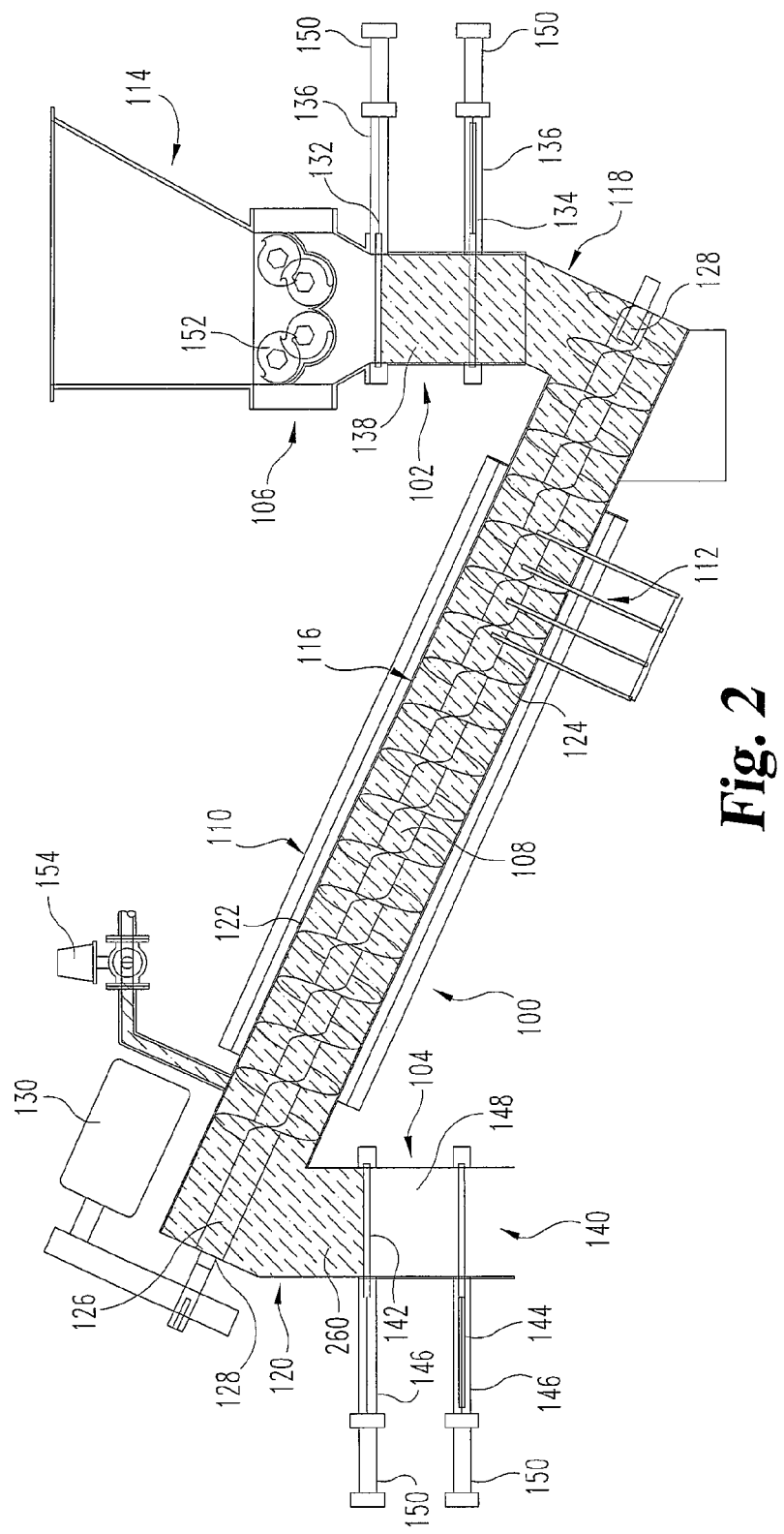
FIG. 2 is a cross-sectional illustrative view of a waste disposal system with an inlet pressure lock having a closed top inlet valve and an open bottom inlet valve and a discharge pressure lock having a closed top discharge valve and an open bottom discharge valve.

During operation of the waste disposal system, when in the first configuration (FIG. 1), a uniform pressure region 160 is maintained between the discharge pressure lock 104 and the chamber 100. In this configuration, shredded waste material can accumulate on a surface of the bottom inlet valve 134. At the same time, treated waste material can be deposited on a surface of the bottom discharge valve 144 via conveyor 108. At an appropriate time, the system can be transitioned from the first configuration to the second configuration (FIG. 2). In the second configuration (FIG. 2), a uniform pressure region 260 is maintained between the chamber 100 and the interior 138 of the inlet pressure lock 102. In this configuration, waste material can pass from within the discharge pressure lock 104 through the discharge exit 140. Similarly, waste material can pass from within the inlet pressure lock 102 through the inlet opening 118 to engage the conveyor 108. At the same time, waste material can collect on a surface of the top inlet valve 132. The conveyor 108 transports the waste material through the enclosure 116 to the discharge opening 120 where it collects on a surface of the top discharge valve 142. When a sufficient quantity of waste material has accumulated at the top discharge valve 142 and/or at the top inlet valve 132, the waste disposal system can be transitioned from the second configuration (FIG. 2) to the first configuration (FIG. 1). The process can then be repeated.

The configuration of valves in the inlet pressure lock 102 and the discharge pressure lock 104 allow the waste disposal system to be operated continuously without interrupting the flow of waste through the system. When the waste disposal system is in the first configuration (FIG. 1), waste material can enter the inlet pressure lock 102 simultaneously and/or at the same rate as it enters the discharge pressure lock 104. In the second configuration, waste material can be discharged from the inlet pressure lock 102 through the inlet opening 118 simultaneously or at the same rate that treated waste material is discharged from the discharge pressure lock 104 through the discharge exit 140. The conveyor 108 can continue transporting waste material through the enclosure 116 even while the system transitions between the first and second configurations.

The top and bottom valves of the inlet pressure lock 102 and the discharge pressure lock 104 can be operated in a cooperative unison fashion. For example, the waste disposal system can be altered from the first configuration to the second configuration by first closing the top inlet valve 132 simultaneously while closing the top discharge valve 142. Alternatively, the top valves can be operated in series. The bottom inlet valve 134 can be opened simultaneously while opening the bottom discharge valve 144. Alternatively, the bottom valves can be operated in series. This cooperative operation ensures that a pressure differential is maintained between the chamber 100 and the exterior atmosphere. Simultaneous operation of the top and the bottom valves cooperatively can also allow the cumulative volume of the chamber 100 to remain constant throughout operation of the waste disposal system.

The waste material is altered and treated at several points while travelling through the waste disposal system. In an optional first step, waste material can be processed by the shredder 106. Waste material is first introduced into the feed hopper 114, which can be in a variety of forms, such as bagged or containerized biomaterials for example. The necked down portion of the feed hopper 114 channels the waste into the shredder 106. The shredder 106 performs various functions. The rotating cutters 152 in the shredder 106 operate cooperatively to physically rend the waste material. The shredder 106 removes any packaging from around the waste material and shreds the packaged waste. The shredder 106 breaks down the waste material into smaller pieces having a relatively homogenous particle size, which increases the amount of exposed surface area of the waste material. The shredding process can be enhanced by providing a pneumatically operated ram or other assistance device which applies downward pressure to waste material in the feed hopper 114 causing it to engage more forcefully with the rotating cutters 152.

The system allows for optional chemical treatment of the waste material. An odor control solution can be added at several points to the waste material. The heated atmosphere and optional direct impingement of steam to the waste material in the chamber 100 helps to ensure complete destruction of live microorganisms. Moisture introduced into the waste material by direct steam impingement can be removed by dehydration.

Waste material is delivered to an end of the conveyor by gravity from the inlet pressure lock 102 through the inlet opening 118. When rotating, the conveyor 108 transports waste material (a function of the helical shape of the conveyor) from the inlet opening 118 through the enclosure 116 to the discharge opening 120. The conveyor 108 both transports and mixes waste material to enhance permeation of the waste material by steam.

Steam is applied to the waste material at various points along the length of the conveyor 108 through the injectors 112. Additionally, heat is supplied by the steam jacket 110. The steam is maintained at or above standard atmospheric pressure, and the temperature is maintained at or above 212° F. The steam jacket 110 is maintained at a temperature such that the surface of the inner wall of the enclosure 116 is held at a temperature at or above 212° F. The combination of the steam jacket 110 and injectors 112 cause the temperature of the waste materials inside of the enclosure 116 to quickly elevate to a temperature equal to or greater than the boiling point of water at any elevation above sea level. The waste material is exposed to the steam via the injectors 112 which protrude in the interior of the enclosure 116.

The mixing action of the conveyor 108 ensures that steam comes into contact with all or substantially all of the surfaces of the waste material, and the heating ensures that infectious microorganisms are killed completely. The conveyor 108 agitates and tumbles the waste material to enhance contact between the steam and the waste material. Similarly, the action of the conveyor 108 ensures good contact between the waste and the heated cylindrical inner wall 122 of the enclosure 116. The close fit of the helical blades of the conveyor 108 to the inner wall of the enclosure 116 ensures that the waste material, at least intermittently, maintains contact with the heated inner wall 122. Mixing tabs (not shown) can be provided on the conveyor 108 to enhance permeation of the waste by the steam. The speed of the conveyor 108 is controlled so that the residence time of the waste material in the chamber 100 is long enough to sufficiently treat the waste material as well as comply with relevant regulations (e.g. 30 minutes).

The steam jacket 110 can provide further treatment of the waste material, including contact with a hot surface so that moisture in the waste material is converted to vapor. The steam jacket 110 can additionally provide a means to dehydrate the waste material, thereby separating recyclable moisture from the waste material and reducing the bulk of the waste material.

The steam is introduced at a pressure which is maintained at sea level atmospheric pressure (~15 psig) so that the corresponding temperature is maintained at or above 212° F. The unique pressure lock system described herein ensures that the pressure within the steam chamber can be maintained consistently while simultaneously introducing and removing waste material from the steam chamber. This is advantageous particularly for applications at elevated altitudes (e.g. certain locations in Colorado) where the atmospheric boiling point temperatures is reduced relative to atmospheric pressure at sea level. The waste disposal system is uniquely suited to operate at elevated temperatures while complying with current regulations (e.g. 212° F. for 30 minutes). Because the steam is maintained near 15 psig, the waste disposal system does not require an ANSI rated high pressure vessel.

The pressure relief valve 154 assists in controlling the pressure within the chamber 100. During operation of the waste disposal system, energy is added to the system through use of the injectors 112. The pressure within the chamber 100 is controlled and maintained through use of the pressure relief valve 154. The pressure relief valve 154 expels air or steam if the internal pressure of the chamber 100 exceeds a predetermined threshold limit, for example 15 psig.

Treated waste material is expelled through the discharge exit 140. The discharge can include a flapper valve connected to a counterweight that normally maintains the discharge opening 120 in a closed condition. As waste material accumulates within the discharge exit 140, the flapper opens under the weight of the waste material permitting the waste material to be discharged to a suitable discharge area such as a conveyor belt or compactor. From there, treated waste material can be transported safely to a landfill or any other suitable disposal site.

The waste disposal system can include any number of sensors which can monitor the temperature, pressure, and other conditions at various points within the system. For example, the steam temperature in the steam jacket 110 can be controlled by a thermocouple (not shown) which is located on or within the steam jacket 110 and operates a valve to control the flow of steam. Additionally, thermocouples can be provided on the surface of the enclosure 116. The thermocouples can operate a valve (not shown) which controls the flow of steam to maintain the temperature of the waste material at the requisite 212° F.

Figure 3:
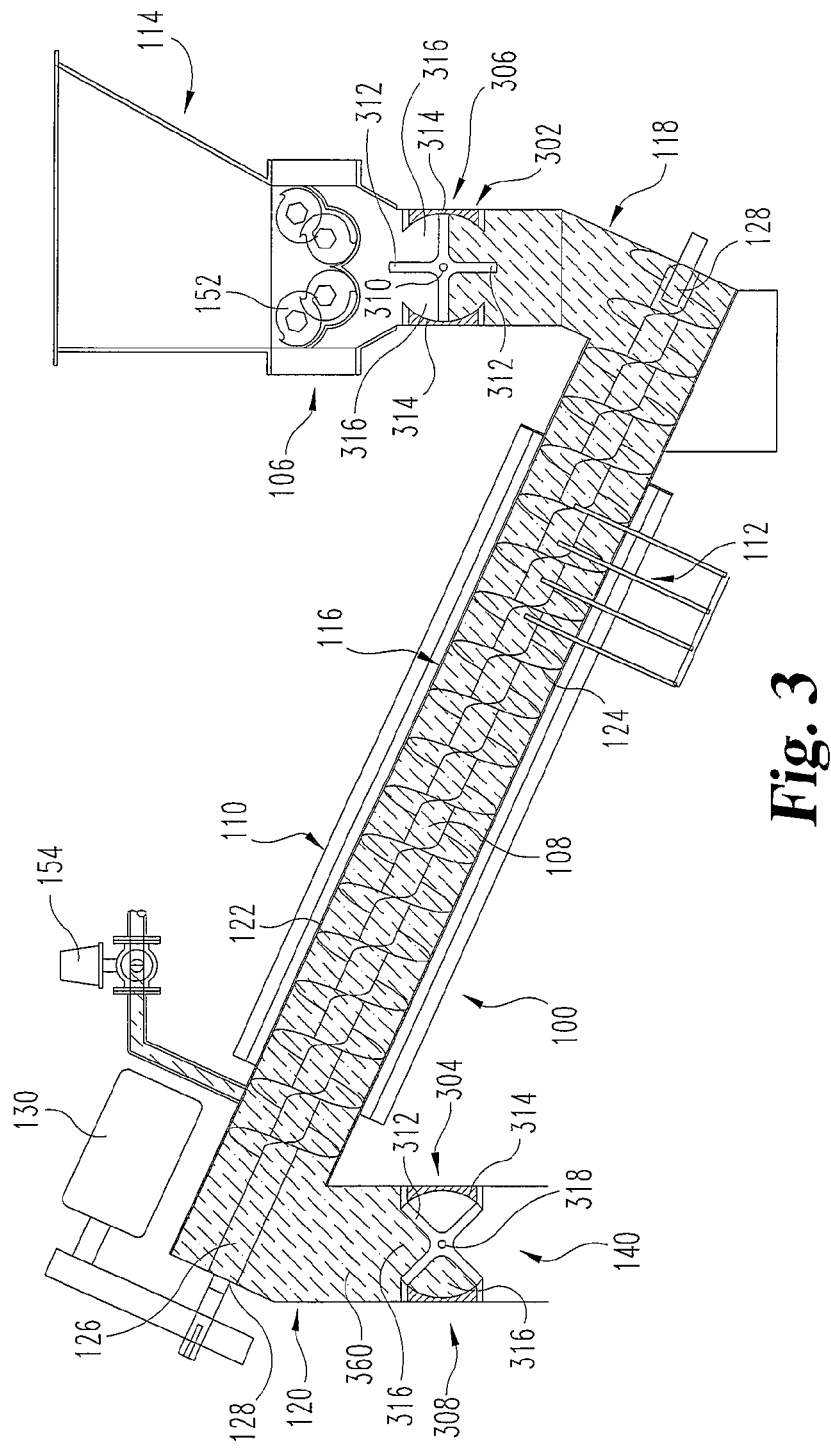
FIG. 3 is a cross-sectional illustrative view of an alternative example of a waste disposal system with an inlet pressure lock having a rotary valve and a discharge pressure lock having a rotary valve.
Figure 4:
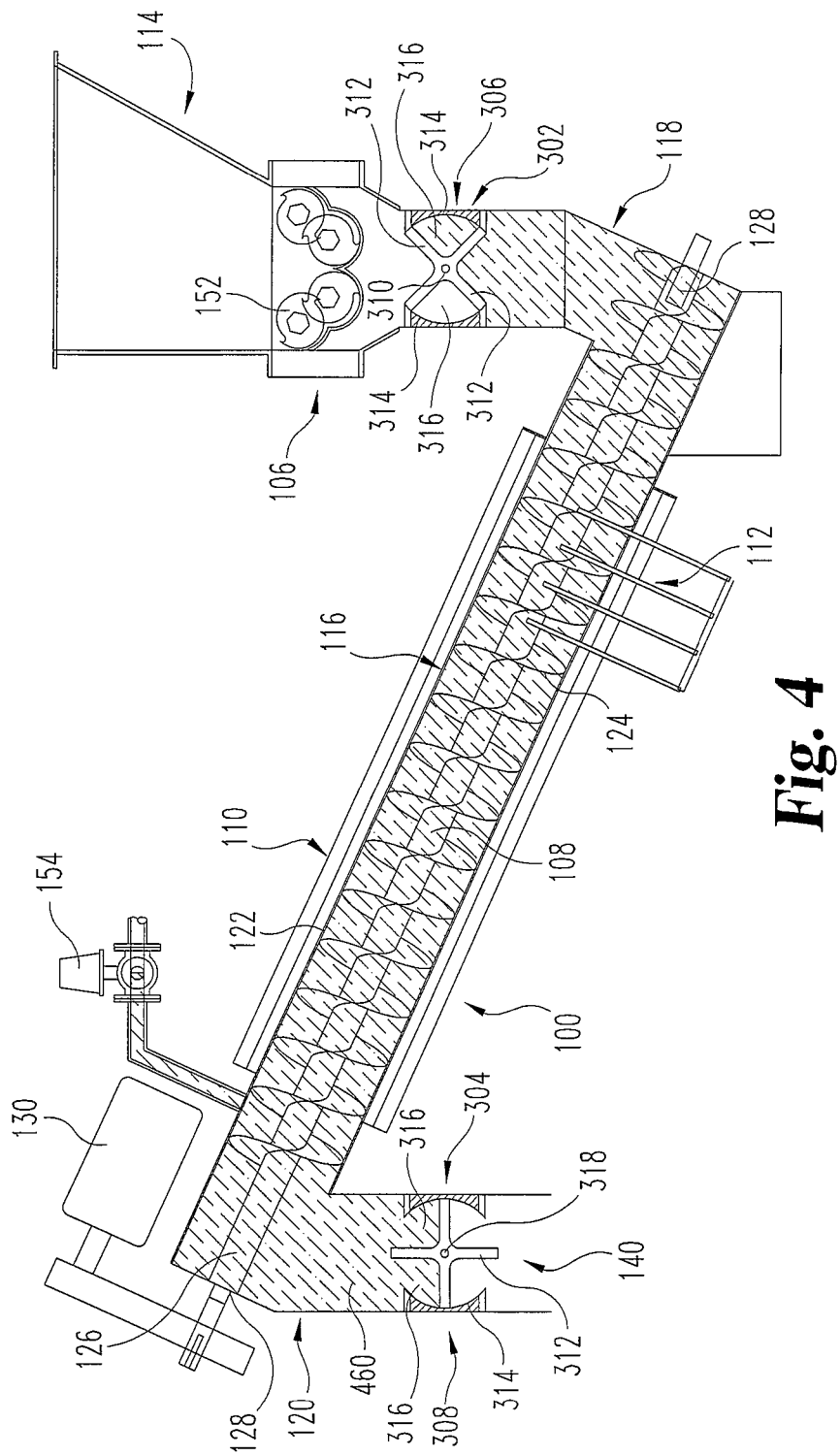
FIG. 4 is a cross-sectional illustrative view of the example of FIG. 3 showing rotary valves in an alternative configuration.

An alternative example of the waste disposal system is shown in FIGS. 3 and 4. The waste disposal system operates in the same manner as previously disclosed with the exception of the inlet and discharge pressure locks. The waste disposal system has an inlet pressure lock 302 and a discharge pressure lock 304. The inlet pressure lock 302 includes an inlet rotary valve 306, and the discharge pressure lock 304 includes a discharge rotary valve 308. The rotary valves provide a similar function as the inlet and discharge valves of the example of FIGS. 1 and 2.

The rotary valves 306 and 308 can be any of a variety of designs. In the FIG. 3 example, the inlet rotary valve 306 has a portion which is rotatable about an axis 310 and is positionable in a variety of rotational positions about the axis 310. The inlet rotary valve 306 has four blades 312. The blades 312 are configured to sealingly interact with curved surfaces 314. At any point during rotation of the inlet rotary valve 306 at least two blades 312 sealingly interact with the curved surfaces 314 such that the chamber 100 is at all times fluidly sealed from the exterior atmosphere. In a first configuration (FIG. 3), at least two of the blades 312 are oriented in a substantially vertical orientation and waste material accumulates in two of four compartments 316 which are defined by the intersection of the blades 312. As the blades 312 are rotated (in this case, for example, in a counterclockwise direction relative to the viewing angle of FIG. 3) from the first configuration to a second configuration (FIG. 4), two compartments 316 become fluidly isolated from the chamber 100 as well as the exterior atmosphere. The isolated compartments 316 are bounded by the curved surfaces 314 as well as the blades 312. One of the isolated compartments 316 that was previously exposed to the shredder outlet contains waste material and has a pressure equal to the pressure of the exterior atmosphere. The other isolated compartment 316 was previously exposed to the inlet opening 118, contains no waste material, and has a pressure equal to the interior pressure of the chamber 100.

As the blades 312 are further rotated (from the FIG. 4 configuration to the FIG. 3 configuration), the accumulated waste material is transported along the curved surface 314 until one of the blades 312 clears the surface 314 whereby the compartment 316 becomes pressurized consistent with the interior pressure 360 (FIG. 3) of the chamber 100, and the waste material is deposited through the inlet opening 118. Simultaneously, an adjacent compartment 316 receives waste material which is then transported along the curved surface 314 and the process is repeated.

The discharge rotary valve 308 operates in a similar manner as inlet rotary valve 306, and includes blades 312 which are rotatable about an axis 318. The discharge rotary valve 308 receives waste material at the interior pressure 460 of the chamber 100 (FIG. 4). As the blades 312 of the discharge rotary valve 308 are rotated, waste material accumulates in one of four compartments 316. As the blades 312 are further rotated, the accumulated waste material is transported within one of the compartments 316 along one of the curved surfaces 314 until one of the blades 312 clears the surface 314. The compartment 316 then becomes pressurized consistent with the exterior atmospheric pressure, and the waste material is deposited through the discharge exit 140.

The rotary valves 306 and 308 can be operated simultaneously in any manner that allows continuous operation of the conveyor 108. The rotary valves 306 and 308 can be rotatably driven by an electric drive motor or any of a variety of suitable motion driving devices (not shown). With the exception of the rotary valves 306 and 308, the example waste disposal system of FIGS. 3 and 4 operates in a similar manner to the waste disposal system disclosed previously and shown in FIGS. 1 and 2. The configuration of FIG. 3 corresponds with the configuration of FIG. 1, and the configuration of FIG. 4 corresponds with the configuration of FIG. 2.

The rotary valves 306 and 308 are not limited to the structure described herein and can be any of a variety of industrial rotary valves which are known in the art and suitable for the present application. Such valves are available and capable of providing a fluid seal as described herein. Other valve types and configurations, in addition to the sliding valves and rotary valves described herein, are envisioned as part of this disclosure. As one non-limiting example, the sliding valves could each individually be replaced with butterfly valves.

Various modifications can be made to the waste disposal system described herein. For example, the conveyor 108 can include a belt type conveyor or two or more sections which are separately controlled. Other design choices such as alternative materials and dimensions are included within the scope of this disclosure.

While the disclosure has been illustrated and described in detail in the drawings and foregoing description, the same is to be considered as illustrative and not restrictive in character, it being understood that only the preferred example has been shown and described and that all changes, equivalents, and modifications that come within the spirit of the inventions defined by the following claims are desired to be protected.

The invention claimed is:

1. A waste disposal system for disposing of waste materials comprising:
    an elongated enclosure having an interior and including an inlet opening at one end and a discharge opening at another end, said enclosure being positioned with the discharge opening being higher than the inlet opening;
    a conveyor positioned between the inlet opening and the discharge opening;
    a steam source and a conduit connected from the steam source to the interior of the enclosure;
    an inlet pressure lock chamber positioned adjacent to the inlet opening, the inlet pressure lock chamber including a top inlet valve and a bottom inlet valve, the bottom inlet valve being slidably positioned adjacent to the inlet opening; and
    a discharge pressure lock chamber positioned adjacent to the discharge opening of the conveyor, the discharge pressure lock chamber having a discharge exit, the discharge pressure lock chamber including a top discharge valve slidably positioned adjacent to the discharge opening of the conveyor and a bottom discharge valve slidably positioned adjacent to the discharge exit.

2. The waste disposal system of claim 1, wherein the bottom inlet valve is slidable between an open position and a closed position;
    wherein when in the closed position the interior is fluidly sealed from the inlet pressure lock chamber; and
    wherein when in the open position the inlet pressure lock chamber is fluidly connected with the interior.

3. The waste disposal system of claim 1, wherein the top inlet valve is slidable between an open position and a closed position;
    wherein when in the closed position the inlet pressure lock chamber is fluidly sealed from the exterior atmosphere; and
    wherein when in the open position the inlet pressure lock chamber is fluidly connected with the exterior atmosphere.

4. The waste disposal system of claim 1, wherein the top discharge valve is slidable between an open position and a closed position;
    wherein when in the closed position the discharge pressure lock chamber is fluidly sealed from the interior; and
    wherein when in the open position the discharge pressure lock chamber is fluidly connected with the interior.

5. The waste disposal system of claim 1, wherein the bottom discharge valve is slidable between an open position and a closed position;
    wherein when in the closed position the discharge pressure lock chamber is fluidly sealed from the exterior atmosphere; and
    wherein when in the open position the discharge pressure lock chamber is fluidly connected with the exterior atmosphere.

6. The waste disposal system of claim 1, wherein the inlet pressure lock chamber includes a rotary valve.

7. The waste disposal system of claim 6, wherein the rotary valve is rotatable about an axis through a plurality of rotational positions;
    wherein in each rotational position the rotary valve provides a fluid seal between the interior and the exterior atmosphere;
    the rotary valve further comprising a compartment for receiving waste material; and wherein during rotation the compartment carries waste material rotationally about the axis from the exterior atmosphere to the interior.

8. The waste disposal system of claim 1, wherein the discharge pressure lock chamber includes a rotary valve.

9. The waste disposal system of claim 8, wherein the rotary valve is rotatable about an axis through a plurality of rotational positions;
   wherein in each rotational position the rotary valve provides a fluid seal between the interior and the exterior atmosphere;
   the rotary valve further comprising a compartment for receiving waste material; and
   wherein during rotation the compartment transports waste material rotationally about the axis from the interior to the exterior atmosphere.

10. The waste disposal system of claim 1, wherein the conveyor is an auger-type conveyor having helical blades.

11. The waste disposal system of claim 1, further comprising a steam jacket positioned circumferentially around a portion of an outside surface of the enclosure.

12. The system of claim 1 in which the system has a first condition in which the bottom inlet valve and the bottom discharge valve are in the closed position and the top inlet valve and the top discharge valve are in the open position.

13. The system of claim 12 in which the system has a second condition in which the bottom inlet valve and the bottom discharge valve are in the open position and the top inlet valve and the top discharge valve are in the closed position.

14. The system of claim 12 in which the inlet and discharge valves are operable to move from the first condition to the second condition by first closing the top inlet valve and the top discharge valve, followed by opening the bottom inlet valve and the bottom discharge valve.

* * * * *